United States Patent
Kawaguchi (10) Patent No.: US 6,878,272 B2
(45) Date of Patent: Apr. 12, 2005

(54) DIALYZING APPARATUS

(75) Inventor: Keizoh Kawaguchi, Komaki (JP)

(73) Assignee: Colin Corporation, Komaki (JP)

( * ) Notice: Subject to any disclaimer, the term of this patent is extended or adjusted under 35 U.S.C. 154(b) by 139 days.

(21) Appl. No.: 10/086,811

(22) Filed: Mar. 4, 2002

(65) Prior Publication Data

US 2003/0006175 A1 Jan. 9, 2003

(30) Foreign Application Priority Data

Jul. 3, 2001 (JP) ........................................ 2001-202720

(51) Int. Cl.⁷ .......................... B01D 61/32; B01D 61/28
(52) U.S. Cl. ...................... 210/321.65; 210/85; 210/87; 210/90; 210/96.1; 210/97; 210/109; 210/134; 210/143; 600/485; 600/494; 600/500; 600/546
(58) Field of Search .............................. 210/85, 87, 90, 210/96.1, 97, 102, 109, 134, 143, 321.65; 600/485, 494, 500, 546; 604/4.01, 30, 31

(56) References Cited

U.S. PATENT DOCUMENTS

| 4,324,663 A | 4/1982 | Hirel et al. ................. 210/646 |
|---|---|---|
| 4,718,891 A | 1/1988 | Lipps .......................... 604/31 |
| 6,200,485 B1 | 3/2001 | Kitaevich et al. ........... 210/739 |

FOREIGN PATENT DOCUMENTS

| EP | 0 498 324 A1 | 8/1992 |
|---|---|---|
| EP | 0 956 815 A1 | 11/1999 |
| EP | 0 990 417 A1 | 4/2000 |
| EP | 0 993 803 A1 | 4/2000 |
| JP | 63-294866 A | 12/1988 |
| JP | 05-285218 A | 11/1993 |
| JP | 08-322824 A | 12/1996 |
| JP | 10-165380 A | 6/1999 |
| JP | 11-221275 A | 8/1999 |
| JP | 2001-000540 A | 1/2001 |

Primary Examiner—John Kim
(74) Attorney, Agent, or Firm—Oliff & Berridge, PLC (57) ABSTRACT

A dialyzing apparatus includes a dialyzer which removes water from blood of a patient at a water-remove rate during a dialysis operation, a blood-pressure-change-related-information obtaining device which obtains a plurality of sorts of blood-pressure-change-related information each of which is related to a change of a blood pressure of the patient during the dialysis operation, and a water-remove-rate control device which controls the water-remove rate of the dialyzer, based on the plurality of sorts of blood-pressure-change-related information, according to a predetermined control manner.

6 Claims, 7 Drawing Sheets

DIALYZING APPARATUS

BACKGROUND OF THE INVENTION

1. Field of the Invention

The present invention relates to a dialyzing apparatus which can automatically control a water-remove rate so as to efficiently remove water from blood of a patient, without causing an abrupt blood-pressure decrease in the patient.

2. Related Art Statement

There is known a dialyzing apparatus which artificially removes, by utilizing osmotic-pressure difference or ultrafiltration, urea, uric acid, or creatinine, together with water, from blood of a patient. When the dialyzing apparatus is used, a patient whose blood circulates through the apparatus, and a doctor who observes the patient cannot move away from the apparatus, for at least several hours. Therefore, it is desired to increase the water-remove rate and thereby quickly finish the dialysis operation. However, if the water-remove rate is too high, the patient may fall in a shock. To avoid this, an appropriate water-remove rate is manually set so as to allow a target water amount to be removed for a dialysis duration of from 4 to 5 hours, in view of a standard body weight and a measured body weight of the patient and a water-remove efficiency of a dialyzer, and the water-remove rate is adjusted depending upon a specific condition of the patient. The water-remove rate is defined as an amount of fluid that permeates per unit time from the blood of the patient into the dialyzing fluid present in the dialyzer through the dialysis membrane, and the fluid amount can be changed by changing a pressure difference over the dialysis membrane, e.g., changing a rotation speed of a negative-pressure pump which produces the pressure difference over the dialysis membrane.

However, the above-described adjustment of the water-remove rate needs a skillful medical specialist, such as a doctor, who can adjust the water-remove rate depending upon the specific condition of the patient. Thus, a relatively large number of medical specialists are needed as compared with a number of dialyzing apparatuses used, or a number of patients observed. However, since there is shortage of those medical specialists, the number of dialyzing apparatuses used cannot be easily increased, and each dialysis operation costs high.

SUMMARY OF THE INVENTION

It is therefore an object of the present invention to provide a dialyzing apparatus which can automatically control a water-remove rate so as to efficiently remove water from blood of a patient, without causing an abrupt blood-pressure decrease in the patient.

The above object has been achieved by the present invention according to which there is provided a dialyzing apparatus comprising a dialyzer which removes water from blood of a patient at a water-remove rate during a dialysis operation; a blood-pressure-change-related-information obtaining device which obtains a plurality of sorts of blood-pressure-change-related information each of which is related to a change of a blood pressure of the patient during the dialysis operation; and a water-remove-rate control device which controls the water-remove rate of the dialyzer, based on the plurality of sorts of blood-pressure-change-related information.

Since the blood-pressure-change-related-information obtaining device obtains a plurality of sorts of blood-pressure-change-related information each of which is related to a change (e.g., a decrease) of a blood pressure of the patient during the dialysis operation, and the water-remove-rate control device controls the water-remove rate of the dialyzer based on the plurality of sorts of blood-pressure-change-related information. Thus, the present apparatus can automatically control the water-remove rate so as to efficiently remove water from blood of the patient, without causing an abrupt blood-pressure decrease in the patient. Therefore, a skillful medical specialist such as a doctor need not adjust the water-remove rate so frequently, and consequently only a relatively small number of medical specialists are needed as compared with a number of dialyzing apparatuses used, and additionally each dialysis operation costs low.

Preferably, the blood-pressure-change-related-information obtaining device obtains a blood-flow parameter that reflects a flow rate of a blood of the patient; an autonomic-nerve parameter that reflects an activity of an autonomic nerve of the patient; a blood-vessel parameter that reflects a degree of expansion of a blood vessel of the patient; and a blood-viscosity parameter that reflects a viscosity of the blood of the patient and, based on those parameters, the water-remove-rate control device controls the water-remove rate. Thus, the present apparatus can operate the dialyzer at an appropriate water-remove rate that corresponds to the blood flow rate, autonomic-nerve activity, blood-vessel expansion degree, and blood viscosity of the patient that are closely related to a blood-pressure decrease of the patient during the dialysis operation. Accordingly, the present apparatus can efficiently remove water from the blood of the patient, without causing an abrupt blood-pressure decrease in the patient.

Preferably, the blood-flow parameter is a systemic-circulation blood volume, BV, that is estimated based on a hematocrit (red-blood-cell volume percentage) that is optically detected from the blood circulating during the dialysis operation, or an amplitude, AMP, of a volumetric pulse wave, such as a photoelectric pulse wave, a finger-tip pulse wave, or an impedance pulse wave, that is detected by a sensor which is worn on a skin of the patient.

Preferably, the autonomic-nerve parameter is a low-frequency component, DTLF, of fluctuations of respective blood-pressure values (or respective pulse-wave propagtation velocities or respective pulse-wave propagation times DT) that are determined in synchronism with respective heartbeats of the patient, a high-frequency component, RRHF, of fluctuations of respective pulse-period values that are determined in synchronism with the respective heartbeats of the patient, or a pressoreceptor-reflex sensitivity, RRHF/DTLF, that is defined as a ratio of one of the high-frequency component and the low-frequency component to the other of the high-frequency component and the low-frequency component. The low-frequency component DTLF may be obtained as a 0.04 to 0.15 Hz signal component of the fluctuations that is sufficiently lower than a respiration frequency of the patient. The high-frequency component RRHF may be obtained as a 0.15 to 0.4 Hz signal component of the fluctuations that is in the vicinity of the respiration frequency of the patient.

Preferably, the blood-vessel parameter is an estimated blood-pressure value, $E_{SYS}$, that is determined based on a pulse-wave propagation velocity, PWV, at which a pressure pulse wave propagates through an artery of the patient, in synchronism with each heartbeat of the patient, or a pulse-wave propagation time DT, or a pulse-wave propagation velocity PWV, that is determined by a pulse-wave propagation-velocity determining means in synchronism with each heartbeat of the patient. Preferably, the blood-viscosity parameter is a hematocrit (red-blood-cell volume percentage), HCT, that is optically detected from the blood circulating during the dialysis operation.

Preferably, the water-remove-rate control device comprises a weighted-value determining means for determining, for each of the plurality of sorts of blood-pressure-change-related information, a weighted value corresponding to a change of said each sort of blood-pressure-change-related information; a water-remove-rate-control-amount determining means for determining a water-remove-rate control amount based on a sum of the respective weighted values determined for the plurality of sorts of blood-pressure-change-related information; and a control means for controlling the water-remove rate of the dialyzer, according to the water-remove-rate control amount determined by the water-remove-rate-control-amount determining means. Since the weighted-value determining means determines, for each of the plurality of sorts of blood-pressure-change-related information, a weighted value corresponding to a change of the each sort of blood-pressure-change-related information, and the control means controls the water-remove rate of the dialyzer, according to a water-remove-rate control amount determined based on a sum of the respective weighted values determined for the plurality of sorts of blood-pressure-change-related information. Thus, the present apparatus can more efficiently remove water from the blood of the patient, without causing an abrupt blood-pressure decrease in the patient.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
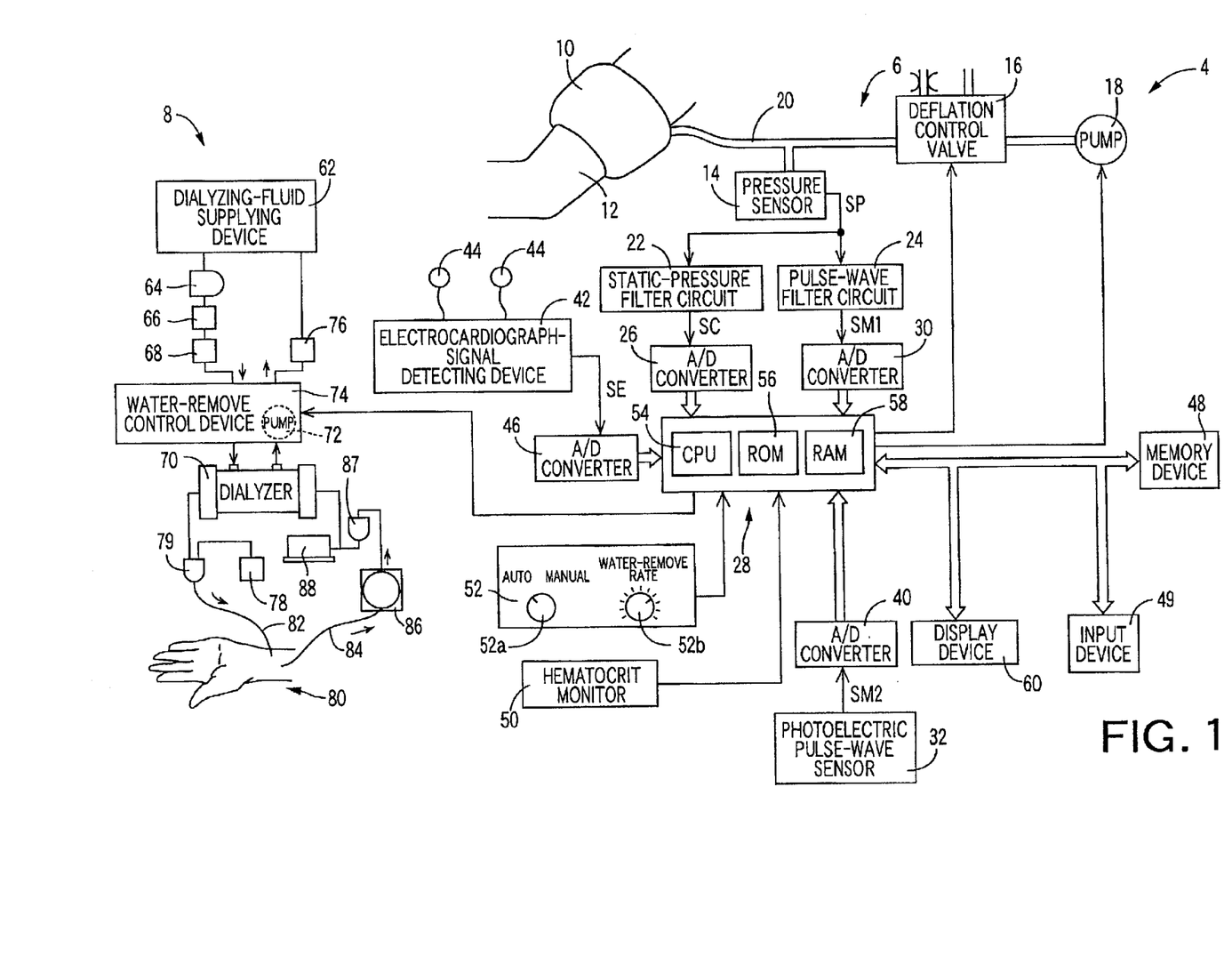
FIG. 1 is a diagrammatic view for explaining a construction of a dialyzing apparatus to which the present invention is applied.

Hereinafter, there will be described an embodiment of the present invention, by reference to the drawings. FIG. 1 is a diagrammatic view for explaining a construction of a dialyzing apparatus 4 to which the present invention is applied. The dialyzing apparatus 4 includes a measurement section 6 and a dialysis section 8. First, the measurement section 6 will be described below.

In FIG. 1, reference numeral 10 designates a blood-pressure measuring cuff which includes a belt-like cloth bag and a rubber bag accommodated in the cloth bag and which is wound around an upper portion 12 of one arm of a patient that is not connected to a dialyzer 70, described later. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure PK in the cuff 10, and supplies a pressure signal SP representing the detected pressure PK, to each of a static-pressure filter circuit 22 and a pulse-wave filter circuit 24. The static-pressure filter circuit 22 includes a low-pass filter and extracts, from the pressure signal SP, a static-pressure component contained in the pressure signal SP, i.e., a cuff pressure signal SC representing the static or pressing pressure in the cuff 10. The cuff pressure signal SC is supplied to a control device 28 via an A/D (analog-to-digital) converter 26. The pulse-wave filter circuit 24 includes a band-pass filter and extracts, from the pressure signal SP, an oscillating component that is produced in synchronism with heartbeat of the patient, i.e., a cuff-pulse-wave signal SM1. The cuff-pulse-wave signal SM1 is supplied to the control device 28 via an A/D converter 30.

Figure 2:
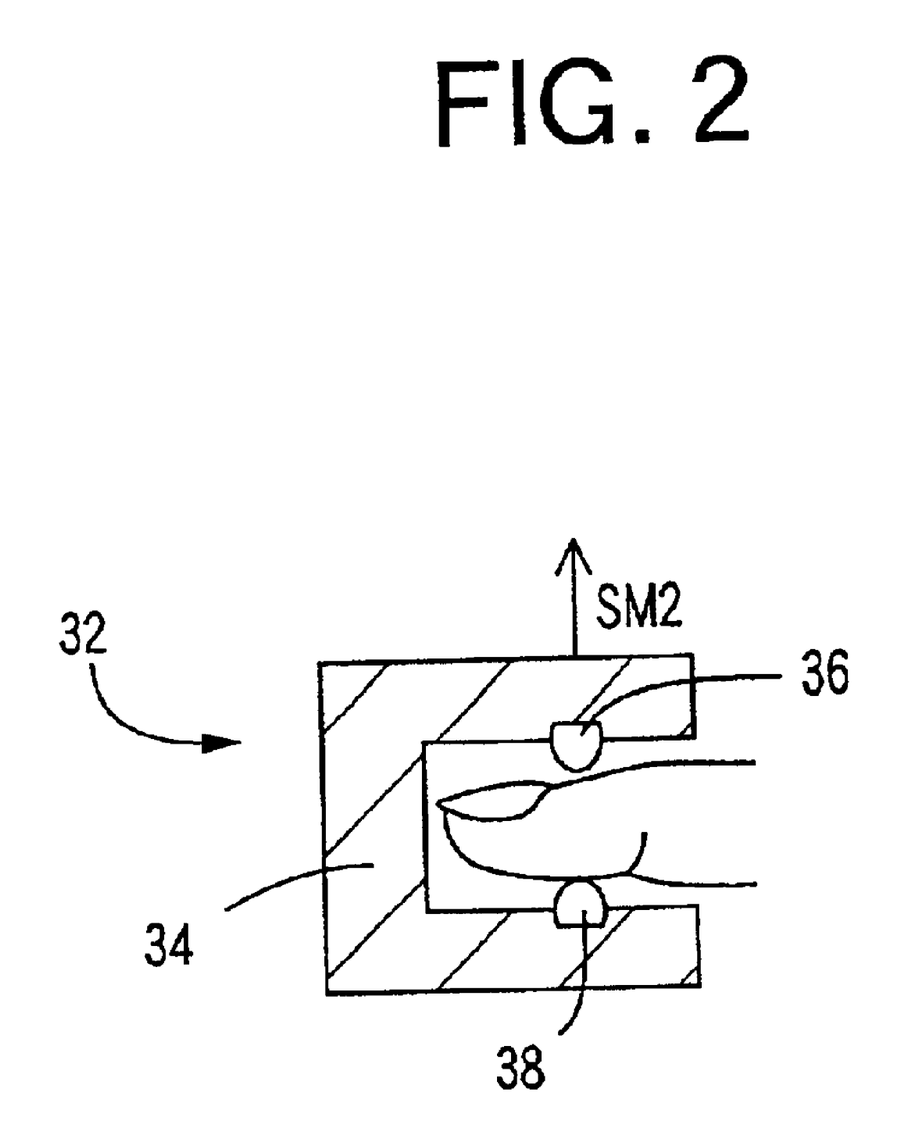
FIG. 2 is a cross-sectional view showing a construction of a photoelectric pulse-wave sensor of the apparatus of FIG. 1.

A photoelectric pulse-wave sensor 32 functions as a volumetric-pulse-wave detecting device. The sensor 32 detects a volumetric pulse wave (i.e., a plethysmograph) representing a volume of blood present in peripheral blood vessels of a living subject. The sensor 32 is worn on, e.g., an end portion of a finger of the other arm than the arm around which the cuff 10 is wound. The photoelectric pulse-wave sensor 32 has the same construction as that of a known sensor used to detect pulse rate or oxygen saturation. As shown in detail in FIG. 2, the sensor 32 includes a housing 34 that can accommodate a portion of a living subject, such as an end portion of a finger; a light emitting element 36 as a light source that is disposed on one of opposite walls of the housing 34 and emits, toward skin of the subject, a red or infrared light in a wavelength range that can be reflected by hemoglobin, preferably a light having a wavelength of, e.g., about 800 nm, that is not influenced by blood oxygen saturation; and a light receiving element 38 that is disposed on the other wall of the housing 34 such that the light receiving element 38 is opposed to the light emitting element 36, and detects the light transmitted through the portion of the subject. The light receiving element 38 produces a photoelectric-pulse-wave signal SM2 representing the detected amount of light, i.e., volume of blood present in capillaries of the portion of the subject, and supplies the photoelectric-pulse-wave signal SM2 to the control device 28 via an A/D converter 40.

An electrocardiograph-signal detecting device 42 continuously detects an electrocardiograph waveform WH, i.e., so-called electrocardiogram (ECG) representing an action potential of cardiac muscle of the subject, through a plurality of electrodes 44 which are adhered to respective prescribed locations of the subject, and supplies an electrocardiograph signal SE representing the detected electrocardiograph waveform WH, to the control device 28 via an A/D converter 56.

A memory device 48 is provided by a well known memory means such as a RAM (random access memory), a magnetic-disc device (HDD), or a removable media (MO, DVD, etc.). The memory device 48 stores a relationship that is used to determine an estimated blood pressure, and a relationship that is used to determine a target water-remove rate. An input device 49 includes various keys that are manually operable by an operator to input an identification (ID) code, a standard body weight, and a measured body weight, of the patient and supply those data to the control device 28. A hematocrit monitor 50 optically measures, during a blood dialysis operation, a hematocrit (red-blood-cell volume percentage %) of the patient, from blood of the patient. A water-remove-rate setting device 52 includes a mode-switch dial 52a that is manually operable to select a manual ("MANUAL") mode or an automatic ("AUTO") mode, and a water-remove-rate dial 52b that is manually operable to set an appropriate water-remove rate of the dialyzer 70. The manual mode allows an operator to manually set a water-remove rate through the water-remove-rate dial 52b, and the automatic mode allows the dialyzing apparatus 4 to automatically set a water-remove rate.

The control device 28 is provided by a so-called microcomputer including a CPU (central processing unit) 54, a ROM (read only memory) 56, a RAM 58, and an I/O port, not shown. The CPU 54 processes signals according to the control programs pre-stored in the ROM 56 by utilizing the temporary-storage function of the RAM 58, and controls the deflation control valve 16 and the air pump 18. In addition, the CPU 54 operates for determining a blood-pressure value BP of the patient, successively determining estimated blood-pressure values EBP of the patient, judging an abnormality of the blood pressure of the patient during a blood dialysis operation, controlling the water-remove rate, and controlling what is displayed by a display device 60. Moreover, the CPU 54 controls respective rotation speeds of a negative-pressure pump 72 of a water-remove control device 74 and a blood-circulation pump 86 of the blood dialysis section 8 that will be described later.

Next, the dialysis section 8 will be described. The dialysis section 8 has a construction similar to that of a common dialyzing device. More specifically described, the dialysis section 8 includes a dialyzing-fluid circulation system as a closed circuit that includes a dialyzing-fluid supplying device 62; a constant-flow-rate valve 64 which adjusts the dialyzing fluid such that the fluid flows at a constant flow rate; a gas-remove tank 66; a warming device 68; the dialyzer 70; the water-remove control device 74 including the negative-pressure pump 72; and a blood-leakage sensor 76. The blood dialysis section 8 additionally includes a blood circulation system as a closed circuit that includes a drip chamber 79 that is connected to the dialyzer 70 and a venous-pressure sensor 78; a tube 82 that is connected to a vein of the patient; a tube 84 that is connected to an artery of the patient; the blood-circulation pump 86; a drip chamber 87; and a heparin injecting pump 88. The dialyzing-fluid supplying device 62 has the function of preparing a dialyzing fluid by mixing a concentrated fluid with water at a prescribed ratio. The warming device 68 keeps the prepared dialyzing fluid at a prescribed temperature. The negative-pressure pump 72 produces a negative pressure in a space between the pump 72 and the supplying device 62, thereby introducing the dialyzing fluid accumulating in the supplying device 62, into the dialyzer 70. The negative-pressure pump 72 additionally adjusts a water-remove rate. The heparin injecting pump 88 injects, little by little, heparin as an anticoagulant into the circulating blood during a blood dialysis operation.

The dialyzer 70 employs a dialysis membrane that is formed of a cellulose material such as regenerated cellulose or acetic cellulose, or a macromolecular material such as polyacrylonitrile copolymer or polymethyl methacrylate, so that the blood and the dialyzing fluid contact each other via the dialysis membrane. Thus, owing to diffusion effect and ultrafiltration effect, waste products and water are moved from the blood of the patient into the dialyzing fluid, and necessary electrolytes are moved from the dialyzing fluid into the blood. The water-remove rate is defined as a difference between the controlled fluid flow-in rate and the fluid flow-out rate, and is expressed as an amount of water removed per unit time. The water-remove rate may be controlled by controlling, e.g., a pressure difference over the dialysis membrane, or controlling a rotation speed of the negative-pressure pump 72 that produces the pressure difference.

Figure 3:
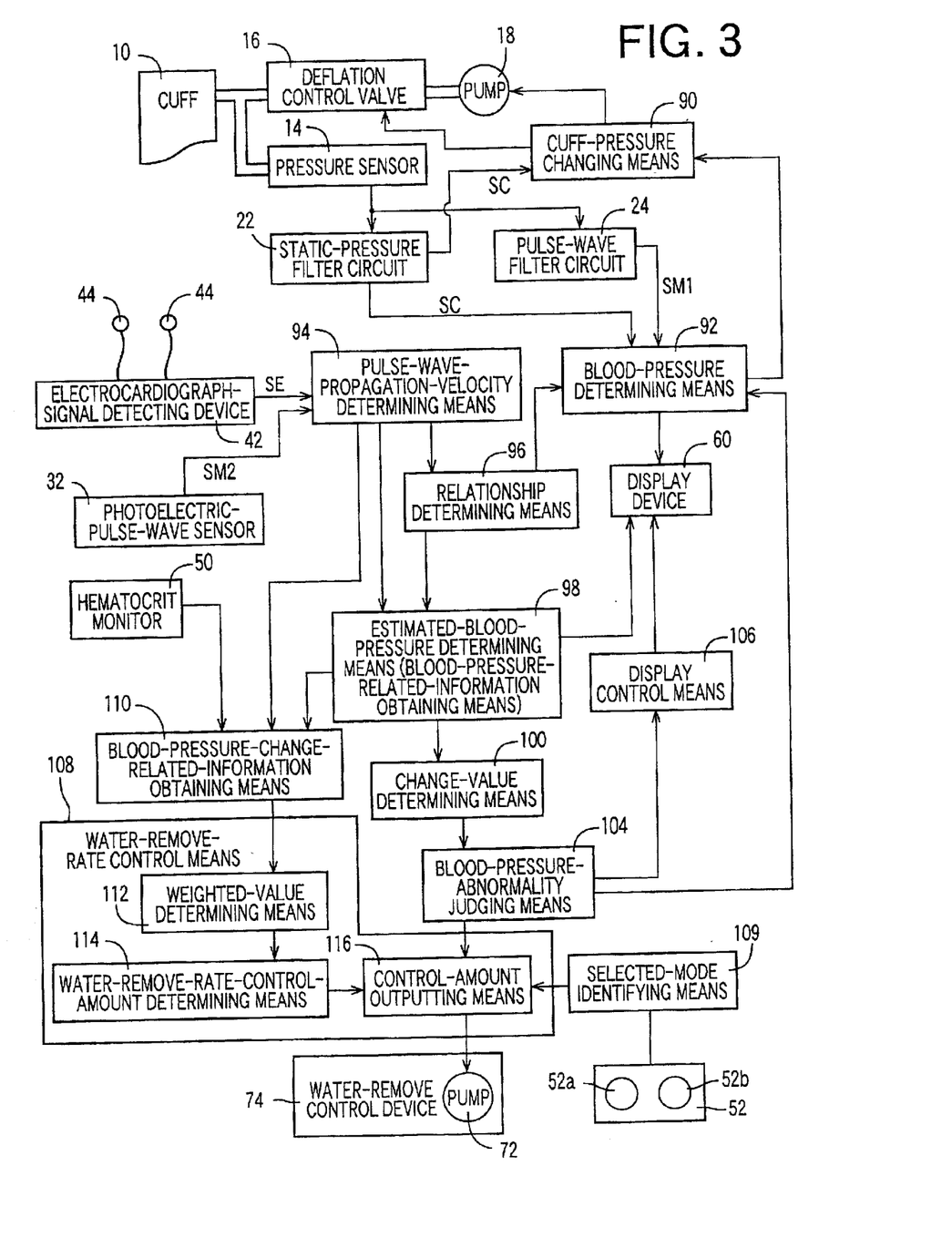
FIG. 3 is a block diagram for explaining essential control functions of a control device of the apparatus of FIG. 1.

FIG. 3 is a block diagram for explaining essential functions of the control device 28. A cuff-pressure changing means 90 and a blood-pressure determining means 92 are operated for carrying out a blood-pressure measuring operation, each time a prescribed blood-pressure-measurement period TB, e.g., several tens of minutes to one hour, passes.

The cuff-pressure changing means 90 operates, based on the cuff pressure signal SC supplied from the static-pressure filter circuit 22, the air pump 18 and the deflation control valve 16 to quickly increase the pressing pressure of the cuff 10, i.e., the cuff pressure PC up to a prescribed target pressure (e.g., 180 mmHg) which would be higher than a systolic blood-pressure value $BP_{SYS}$ of the patient and subsequently slowly decrease the cuff pressure PC at a rate of from 2 to 3 mmHg/sec. After the blood-pressure determining means 92, described below, has determined a blood-pressure value BP of the patient, the cuff-pressure changing means 90 quickly decreases the cuff pressure PC down to atmospheric pressure. The blood-pressure determining means 92 determines a systolic, a mean, and a diastolic blood-pressure value $BP_{SYS}$, $BP_{MEAN}$, $BP_{DIA}$ of the upper arm 12 of the patient, according to well-known oscillometric method, based on the cuff-pressure signal SC continuously supplied from the static-pressure filter circuit 22, and the cuff-pulse-wave signal SM1 continuously supplied from the pulse-wave filter circuit 24, each during the slow decreasing of the cuff pressure PC under the control of the cuff-pressure changing means 90. In addition, the blood-pressure determining means 92 operates the display device 60 to display the thus determined blood-pressure values $BP_{SYS}$, etc.

Figure 4:
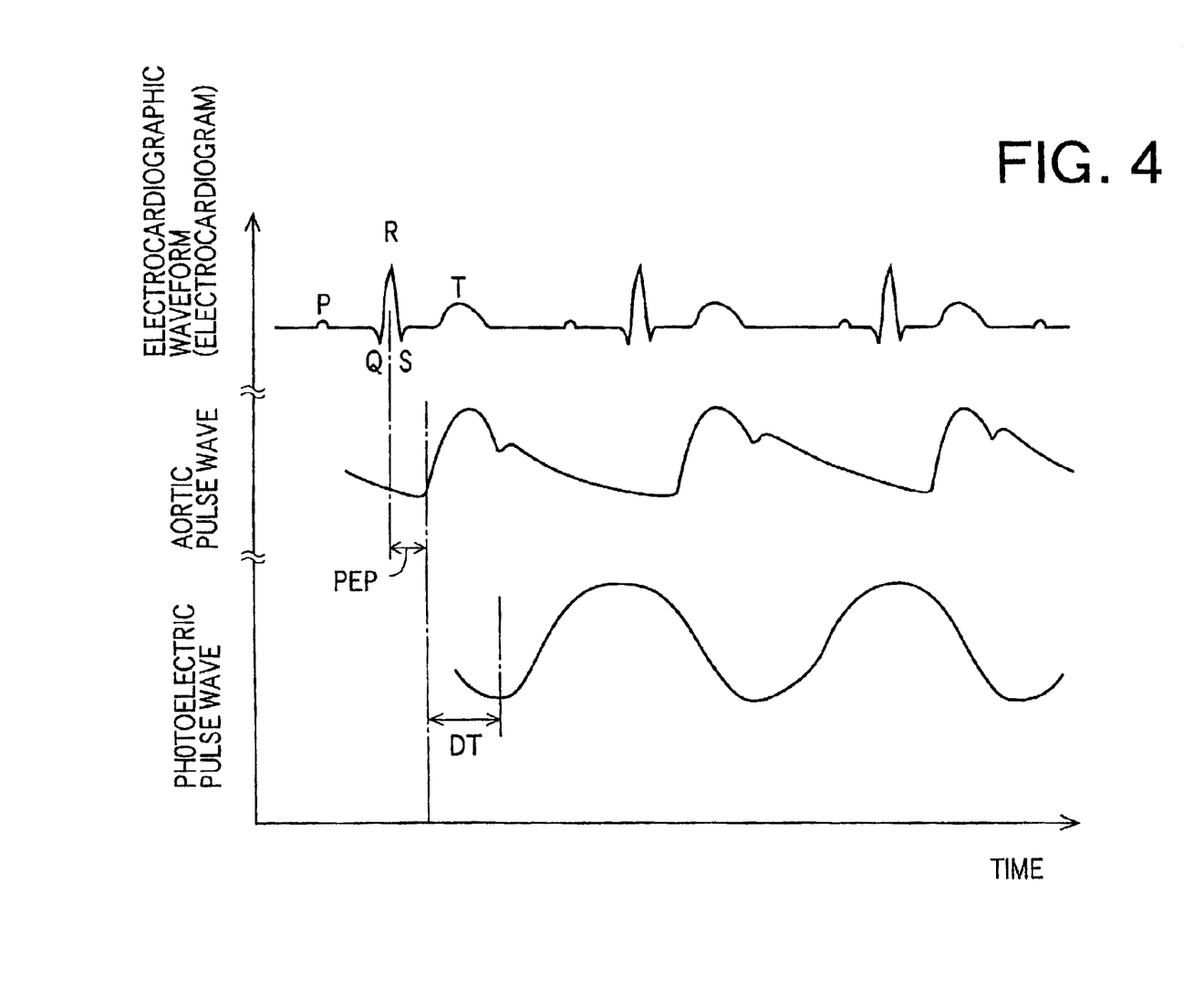
FIG. 4 is a graph for explaining a manner in which a pulse-wave propagation time DT is determined by a pulse-wave-propagation-velocity determining means shown in FIG. 3.

A pulse-wave-propagation-velocity determining means 94 successively determines, as illustrated in FIG. 4, a time difference DT (i.e., a pulse-wave propagation time) between a periodic point (e.g., an R-wave) on each of successive heartbeat-synchronous pulses of the electrocardiographic waveform continuously detected by the electrocardiograph-signal detecting device 42, and a periodic point (e.g., a rising or minimal point) on a corresponding one of successive heartbeat-synchronous pulses of the photoelectric pulse wave continuously detected by the photoelectric pulse-wave sensor 32. The determining means 94 successively determines, based on each of the pulse-wave propagation times DT successively determined for the successive heartbeat-synchronous pulses, a pulse-wave-propagation velocity PWV (m/sec) at which a pulse wave propagates through an artery of the patient, according to the following Expression 1 pre-stored in the ROM 56:

$$PWV=L/(DT-PEP) \quad \text{(Expression 1)}$$

where L (m) is a distance from the left ventricle of the heart, via the aorta, to a position where the sensor 32 is worn on the patient, and PEP (sec) is a pre-ejection period between an R-wave of the electrocardiographic waveform and a rising point of an aortic pulse wave. The distance L (m) is a value actually measured from the patient, or a value converted from a height of the patient, and the pre-ejection period PEP is a value actually measured from the patient, a statistically obtained value, or a value experimentally obtained in advance from the patient.

The pulse-wave propagation time DT, or the pulse-wave propagation velocity PWV determined from the time DT, increases as the blood pressure, or the degree of arteriosclerosis, of the patient increases. Therefore, the time DT or the velocity PWV can be said as a mathematical function of blood pressure or degree of arteriosclerosis. For example, providing that a pulse-wave propagation velocity PWV corresponding to a prescribed blood pressure (e.g., 80 mmHg) is defined as a normalized pulse-wave propagation velocity $PWV_N$, the normalized pulse-wave propagation velocity $PWV_N$ increases as the degree of arteriosclerosis increases. Thus, the normalized pulse-wave propagation velocity $PWV_N$ can be used as very useful arteriosclerosis-related information. The pulse-wave propagation velocity PWV can be used as the normalized pulse-wave propagation velocity $PWV_N$.

A relationship determining means 96 determines coefficients α, β of the following Expression 2 representing a relationship between estimated blood pressure EBP and pulse-wave-propagation velocity PWV, based on one of systolic, mean, and diastolic blood-pressure values $BP_{SYS}$, $BP_{MEAN}$, $BP_{DIA}$ determined by the blood-pressure determining means 92 in a blood-pressure measuring operation, and the pulse-wave-propagation velocity PWV determined by the pulse-wave-propagation-velocity determining means 94 during the blood-pressure measuring operation, or immediately before or after the measuring operation. For example, the coefficients α, β of the Expression 2 are determined based on a first pair of a systolic blood pressure $BP_{SYS}$ determined by the blood-pressure determining means 92 in the current blood-pressure measuring operation and a pulse-wave propagation velocity PWV determined during the current measuring operation, and a second pair of a systolic blood pressure $BP_{SYS}$ determined by the means 92 in the last blood-pressure measuring operation and a pulse-wave propagation velocity PWV determined during the last measuring operation.

$$EBP=\alpha(PWV)+\beta \quad \text{(Expression 2)}$$

where α and β are positive constants.

If the systolic blood-pressure values $BP_{SYS}$ determined by the blood-pressure determining means 92 are used to determine the coefficients of the above-indicated Expression 2, Expression 2 provides estimated systolic blood-pressure values $EBP_{SYS}$; if the mean blood-pressure values $BP_{MEAN}$ determined by the means 92 are used to determine the coefficients of Expression 2, Expression 2 provides estimated mean blood-pressure values $EBP_{MEAN}$; and if the diastolic blood-pressure values $BP_{DIA}$ determined by the means 92 are used to determine the coefficients of Expression 2, Expression 2 provides estimated diastolic blood-pressure values $EBP_{DIA}$. Which sort of blood-pressure values out of the systolic, mean, and diastolic blood-pressure values $BP_{SYS}$, $BP_{MEAN}$, $BP_{DIA}$ determined by the means 92 are selected to determine Expression 2, depends upon which sort of blood-pressure values out of systolic, mean, and diastolic blood-pressure values are continuously monitored as estimated blood-pressure values EBP.

An estimated-blood-pressure determining means 98 functioning as a blood-pressure-related-information obtaining means, successively and non-invasively determines, according to Expression 2 whose coefficients α, β have been determined by the relationship determining means 96, an estimated blood-pressure value EBP of the patient based on each of the pulse-wave-propagation velocities PUV successively determined by the wave-propagation-velocity determining means 94. In addition, the determining means 98 operates the display device 60 to display a time-wise change of the successively determined, estimated blood-pressure values EBP. Preferably, a period at which the determining means 98 determines an estimated blood-pressure value EBP is as short as the period of one heartbeat or several heartbeats, but it may be considerably long if it is shorter than the blood-pressure-measurement period TB of the blood-pressure determining means 92.

A change-value determining means 100 successively determines a change value of each of the estimated blood-pressure values EBP successively determined by the estimated-blood-pressure determining means 98. An estimated-blood-pressure change value means a rate of change, or an amount of change, of each of the successively determined, estimated blood-pressure values EBP from a reference estimated blood-pressure value EBP. The reference estimated blood-pressure value EBP may be an estimated blood-pressure value EBP determined when the current relationship (i.e., the current coefficients of Expression 2) is determined by the relationship determining means 96, that is, the blood-pressure value BP determined by the blood-pressure determining means 92.

A blood-pressure-abnormality judging means 104 judges that a lowering of the blood pressure of the patient is abnormal, when the estimated-blood-pressure change value determined by the change-value determining means 100 is greater than one of a plurality of abnormality-judgment threshold values, selected for the patient by a selecting means (not shown), that corresponds to a time duration which has elapsed from a commencement of the current blood dialysis operation. When the judging means 104 judges that the blood pressure of the patient is abnormal, the judging means 104 operates a display control means 106 to control the display device 60 to indicate the abnormality, and additionally operates the cuff-pressure changing means 90 and the blood-pressure determining means 92 to measure, using the cuff 10, reliable blood-pressure values BP of the patient.

A water-remove-rate control means 108 controls, in a state in which a selected-mode identifying means 109 identifies that the manual mode is selected, the water-remove control device 74 so that the dialyzer 70 removes water at the water-remove rate manually set through the water-remove-rate dial 52b of the water-remove-rate setting device 52. Since the hematocrit (i.e., red-blood-cell volume percentage %) of blood of the patient increases as the blood dialysis (i.e., water removal) advances, the water-remove rate is gradually decreased as time elapses from the commencement of the current dialysis operation or as the hematocrit increases. In addition, the water-remove-rate control means 108 automatically controls, in a state in which the selected-mode identifying means 109 identifies that the automatic mode is selected, the water-remove rate of the dialyzer 70, based on a plurality of sorts of blood-pressure-change-related information each of which is related to a change (e.g., a decrease) of blood pressure of the patient who is undergoing a dialysis operation, so that water can be efficiently removed from the blood of the patient without causing an abrupt blood-pressure decrease in the patient. The plurality of sorts of blood-pressure-change-related information include a blood-flow parameter that reflects a flow amount or rate of blood of the patient; an autonomic-nerve parameter that reflects an activity of the autonomic nerve of the patient; a blood-vessel parameter that reflects a degree of expansion of blood vessels of the patient; and a blood-viscosity parameter that reflects a viscosity of blood of the patient. Moreover, the water-remove-rate control means 108 automatically decreases, by a prescribed value, the water-remove rate effective in the dialysis section 8, or even stops the current water-removing operation, if the blood-pressure-abnormality judging means 104 judges that an amount of lowering of the blood pressure of the patient is abnormal.

A blood-pressure-change-related-information obtaining means 110 obtains a plurality of sorts of blood-pressure-change-related information, e.g., a blood-flow parameter that reflects a flow amount or rate of the blood of the patient 80; an autonomic-nerve parameter that reflects an activity of the autonomic nerve of the patient 80; a blood-vessel parameter that reflects a degree of expansion of blood vessels of the patient 80; and a blood-viscosity parameter that reflects a viscosity of the blood of the patient 80. The blood-flow parameter may be obtained as a systemic circulation blood volume, BV, that is estimated from a hematocrit (i.e., red-blood-cell volume percentage), HCT, optically detected by the hematocrit monitor 50 from the blood circulating during the dialysis operation; or an amplitude, AMP, of a volumetric pulse wave such as a photoelectric pulse wave detected by the photoelectric-pulse-wave sensor 32 worn on the skin of the patient, a finger-tip-portion pulse wave, or an impedance pulse wave. The autonomic-nerve parameter may be obtained as a low-frequency component, DTLF, of fluctuations of respective blood-pressure values, $E_{SYS}$, (or respective pulse-wave propagation velocities or propagation times DT) that are determined by the pulse-wave propagation-velocity determining means 94 in synchronism with respective heartbeats of the patient; a high-frequency component, RRHF, of fluctuations of respective pulse-period values that are determined by the pulse-wave-propagation-velocity determining means 94 in synchronism with the respective heartbeats of the patient; or a pressoreceptor-reflex sensitivity, RRHF/DTLF, that is defined as a ratio of one of the high-frequency component and the low-frequency component to the other of the two components. The low-frequency component DTLF of fluctuations of the blood-pressure values may be obtained as a 0.04 to 0.15 Hz signal component of the fluctuations that is sufficiently lower than a respiration frequency of the patient. The high-frequency component RRHF of fluctuations of the pulse-period values may be obtained as a 0.15 to 0.4 Hz signal component of the fluctuations that is in the vicinity of the respiration frequency of the patient. The blood-vessel parameter may be obtained as respective estimated blood-pressure values $E_{SYS}$ that are determined by the estimated-blood-pressure determining means 98 in synchronism with the respective heartbeats of the patient; or the respective propagation times DT, or respective pulse-wave propagation velocities PW, that are determined by the pulse-wave propagation-velocity determining means 94 in synchronism with the respective heartbeats of the patient. The blood-viscosity parameter may be obtained as the hematocrit (red-blood-cell volume percentage) HCT optically detected by the hematocrit monitor 50 from the blood circulating during the dialysis operation.

The water-remove-rate control means 108 includes a weighted-value determining means 112 which determines, for each of the above-indicated sorts of blood-pressure-change-related information, a weighted value corresponding to an amount of change of the each sort of blood-pressure-change-related information; a water-remove-rate-control-amount determining means 114 which determines a water-remove-rate control amount based on a sum of the respective weighted values determined by the weighted-value determining means 112; and a control-amount outputting means 116 which outputs the water-remove-rate control amount determined by the water-remove-rate-control-amount determining means 114. In the automatic mode, the water-remove-rate control means 108 determines the water-remove-rate control amount based on the blood-flow parameter, the autonomic-nerve parameter, the blood-vessel parameter, the blood-viscosity parameter, an actually measured body weight of the patient, a standard body weight of the patient that is determined based on the height of the patient that is input through the input device 49, and a prescribed water-remove efficiency of the dialyzer 70, according to a prescribed relationship (i.e., a control formula) that is pre-stored in the ROM 56. Based on the thus determined water-remove-rate control amount, the control means 108 changes the water-remove rate of the dialyzer 70.

The above-indicated relationship (i.e., control formula) employed by the water-remove-rate control means 108 is experimentally obtained, in advance, so as to finish a dialysis operation as quickly as possible without causing the patient to fall in a shock (i.e., an abrupt blood-pressure decrease). A decrease in each of the above-described systemic-circulation blood volume BV, the volumetric-pulse-wave amplitude AMP, the low-frequency component DTLF, the pressoreceptor-reflex sensitivity (RRHF/DTLF), the estimated blood-pressure value $E_{SYS}$, and the pulse-wave propagation velocity PW, each as the blood-pressure-change-related information, indicates a decrease of the blood pressure of the patient during the dialysis operation. Therefore, the relationship (i.e., control formula) employed by the water-remove-rate control means 108 is so prescribed as to decrease the water-remove rate by an amount corresponding to a rate or an amount of the decrease. On the other hand, an increase in each of the pulse-wave propagation time DT, the high-frequency component RRHF, and the hematocrit HCT, each as the blood-pressure-change-related information, indicates a decrease of the blood pressure of the patient during the dialysis operation. Therefore, the relationship (i.e., control formula) employed by the water-remove-rate control means 108 is so prescribed as to decrease the water-remove rate by an amount corresponding to a rate or an amount of the increase.

The weighted-value determining means 112 judges whether the rate of change of the systemic-circulation blood volume BV is lower than a lower limit, or is higher than an upper limit, of a predetermined range of, from −5% to +5% and, if the rate of change is lower than the lower limit of −5%, gives a weighted value of, e.g., −5 and, if the rate of change is higher than the upper limit of 5%, gives a weighted value of, e.g., 5. In addition, the weighted-value determining means 112 judges whether the rate of change of the volumetric-pulse-wave amplitude AMP is lower than a lower limit, or is higher than an upper limit, of a predetermined range of, from −10% to +10% and, if the rate of change is lower than the lower limit of −10%, gives a weighted value of, e.g., −1 and, if the rate of change is higher than the upper limit of 10%, gives a weighted value of, e.g., 1. The weighted-value determining means 112 judges whether the rate of change of the low-frequency component DTLF is lower than a lower limit, or is higher than an upper limit, of a predetermined range of, from −10% to +10% and, if the rate of change is lower than the lower limit of −10%, gives a weighted value of, e.g., −2 and, if the rate of change is higher than the upper limit of 10%, gives a weighted value of, e.g., 2. The weighted-value determining means 112 judges whether the rate of change of the pressoreceptor-reflex sensitivity (RRHF/DTLF), BRS, is lower than a lower limit, or is higher than an upper limit, of a predetermined range of, from −10% to +10% and, if the rate of change is lower than the lower limit of −10%, gives a weighted value of, e.g., −2 and, if the rate of change is higher than the upper limit of 10%, gives a weighted value of, e.g., 2. The weighted-value determining means 112 judges whether the rate of change of the estimated blood-pressure value $E_{SYS}$ is lower than a lower limit, or is higher than an upper limit, of a predetermined range of, from −25% to +25% and, if the rate of change is lower than the lower limit of −25%, gives a weighted value of, e.g., −5 and, if the rate of change is higher than the upper limit of 25%, gives a weighted value of, e.g., 5. The weighted-value determining means 112 judges whether the rate of change of the high-frequency component RRHF is lower than a lower limit, or is higher than an upper limit, of a predetermined range of, from −10% to +10% and, if the rate of change is lower than the lower limit of −10%, gives a weighted value of, e.g., +2 and, if the rate of change is higher than the upper limit of 10%, gives a weighted value of, e.g., −2. The weighted-value determining means 112 judges whether the rate of change of the hematocrit HCT is lower than a lower limit, or is higher than an upper limit, of a predetermined range of, from −5% to +5% and, if the rate of change is lower than the lower limit of −5%, gives a weighted value of, e.g., +5 and, if the rate of change is higher than the upper limit of 5%, gives a weighted value of, e.g., −5. Finally, the weighted-value determining means 112 calculates an evaluation value, P, equal to a sum of the respective weighted values determined for the respective rates of change of the above-described parameters.

The water-remove-rate-control-amount determining means 114 determines a water-remove-rate control amount based on the evaluation value P determined by the weighted-value determining means 112. For example, the determining means 114 determines within which one of a plurality of predetermined evaluation-value ranges the evaluation value P falls, and determines, as the water-remove-rate control amount, one of a plurality of predetermined water-remove-rate change amounts that corresponds to the determined evaluation-value range. More specifically described, if the evaluation value P is not greater than a second lower-limit judgment value, e.g., −20, the determining means 114 determines, as the water-remove-rate control amount, a predetermined decrease amount, e.g., −0.2 l/h; if the evaluation value P is greater than the second lower-limit judgment value and not greater than a first lower-limit judgment value, e.g., −10, the determining means 114 determines, as the water-remove-rate control amount, a predetermined decrease amount, e.g., −0.1 l/h; if the evaluation value P is greater than the first lower-limit judgment value (e.g., −10) and is not greater than a first upper-limit judgment value, e.g., +10, the determining means 114 determines zero as the water-remove-rate control amount; if the evaluation value P is greater than the first upper-limit judgment value, e.g., +10, and not greater than a second upper-limit judgment value, e.g., +20, the determining means 114 determines, as the water-remove-rate control amount, a predetermined increase amount, e.g., +0.1 l/h; and if the evaluation value P is greater than the second upper-limit judgment value, e.g., +20, the determining means 114 determines, as the water-remove-rate control amount, a predetermined increase amount, e.g., +0.2 l/h.

The control-amount outputting means 116 outputs the water-remove-rate control or change amount determined by the water-remove-rate-control-amount determining means 114, so that the actual water-remove rate of the dialyzer 70 is changed according to the water-remove-rate change amount. For example, if the water-remove-rate-control-amount determining means 114 determines the water-remove-rate increase amount, e.g., +0.2 l/h for the current water-remove rate, e.g., 15 l/h, the current water-remove rate is changed to 15.2 l/h.

The display control means 106 also functions as a water-remove-rate displaying means for operating the display device 60 to display the water-remove-rate control or change amount determined by the water-remove-rate-control-amount determining means 108, and the actual water-remove rate changed according to the water-remove-rate change amount. Thus, a medical staff can judge, from what is displayed by the display device 60, whether the water-remove rate of the present dialyzing apparatus 4 is properly controlled. That is, a single medical staff can easily monitor a plurality of dialyzing apparatuses 4.

Figure 5:
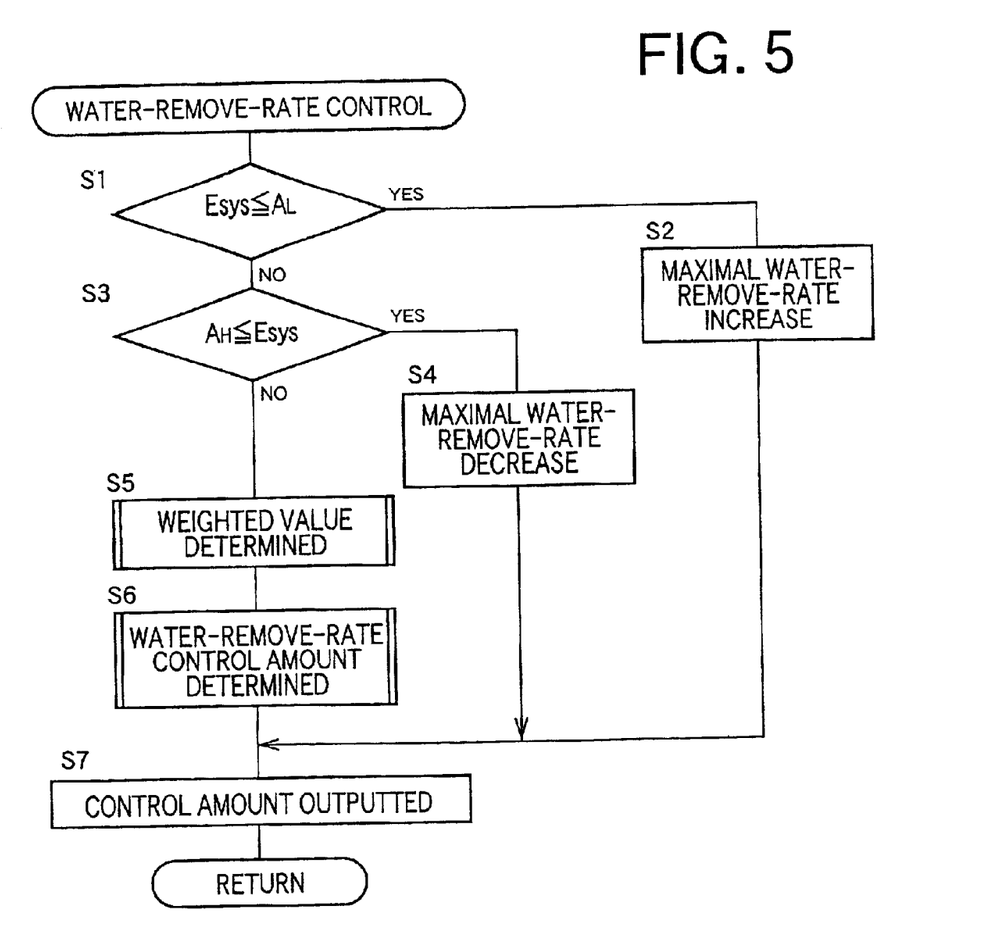
FIG. 5 is a flow chart representing a control program according to which the control device shown in FIG. 1 is operated, i.e., a water-remove-rate control routine.
Figure 6:
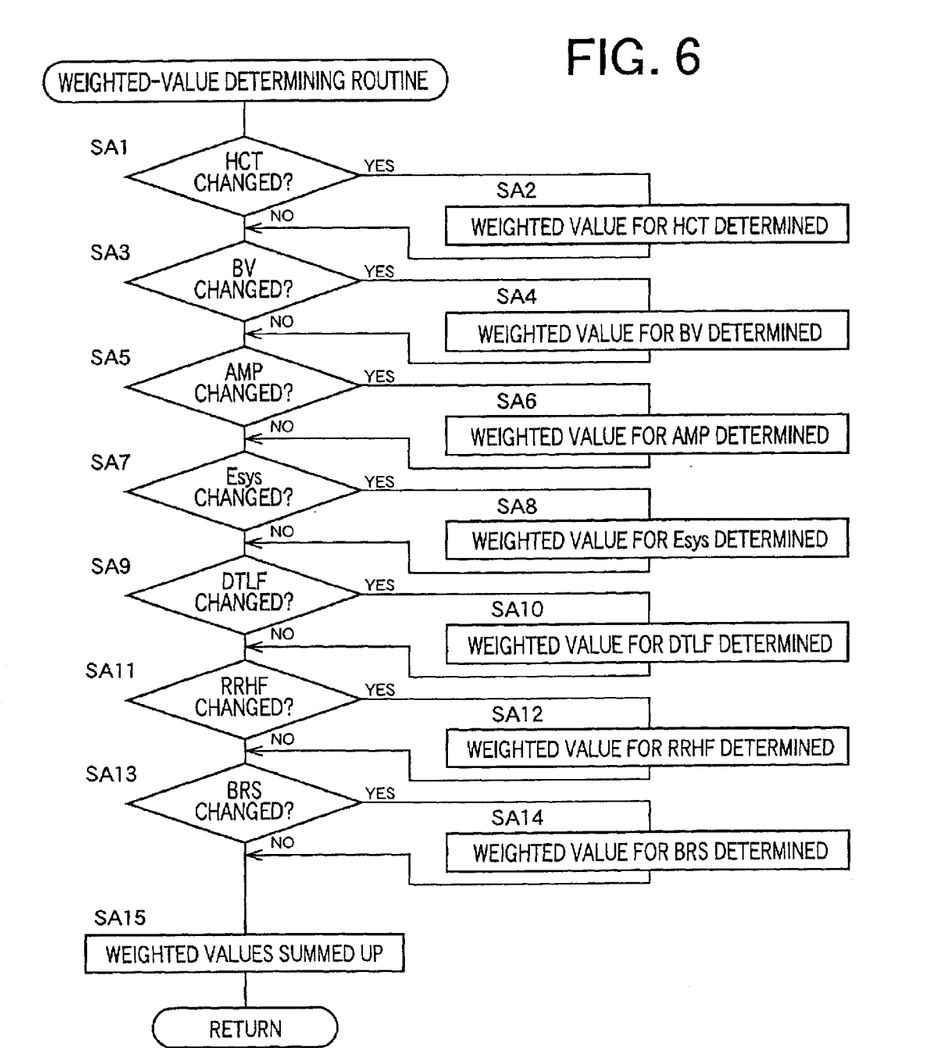
FIG. 6 is a flow chart representing another control program according to which the control device shown in FIG. 1 is operated, i.e., a weighted-value determining routine.
Figure 7:
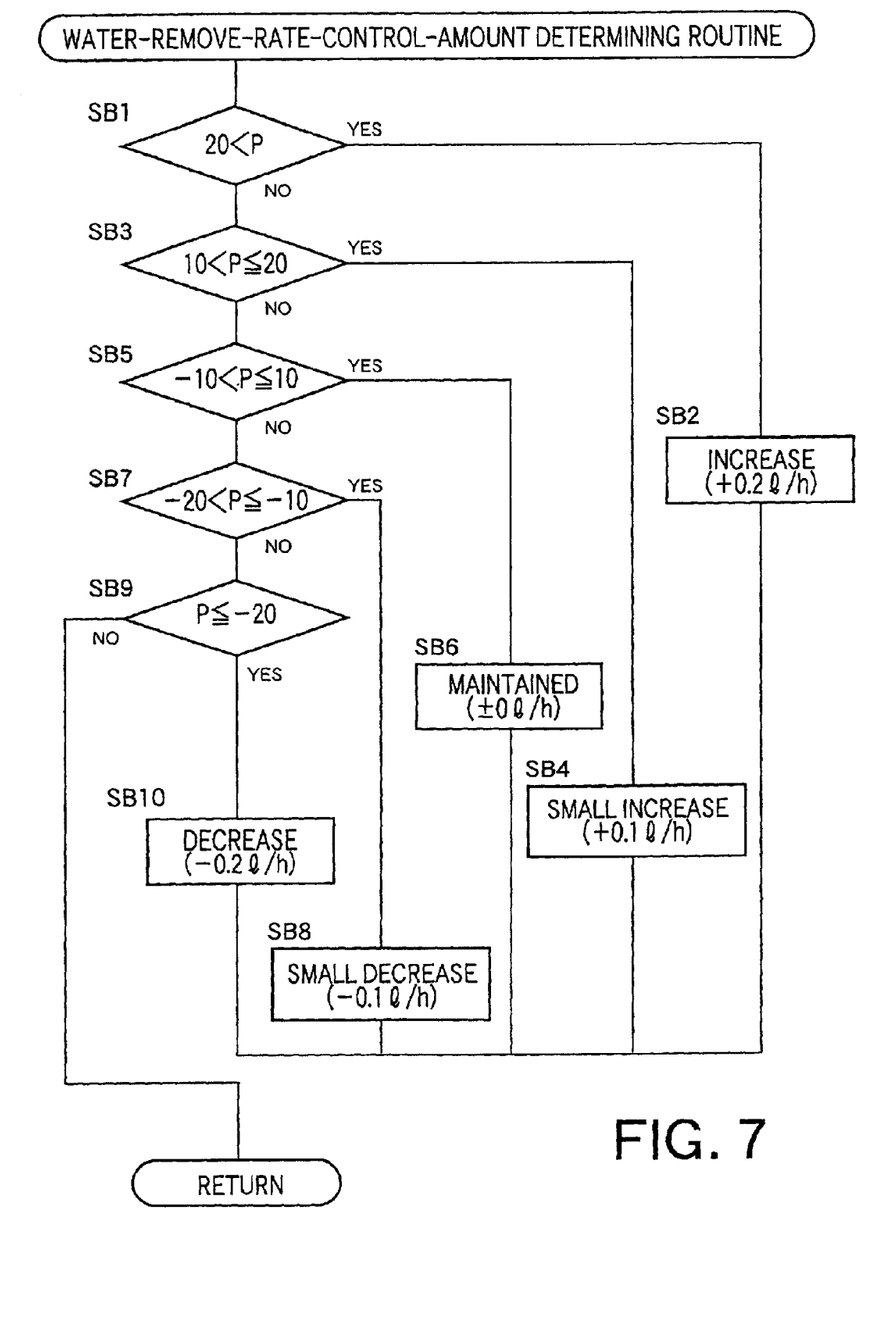
FIG. 7 is a flow chart representing another control program according to which the control device shown in FIG. 1 is operated, i.e., a water-remove-rate-control-amount determining routine.

FIGS. 5, 6, and 7 are flow charts for explaining the essential control functions of the control device 28 that are periodically implemented at a prescribed period of from several milliseconds to several tens of milliseconds, in the state in which the automatic mode is selected. More specifically described, FIG. 5 shows a water-remove-rate control routine; FIG. 6 shows a water-remove-rate-control-amount determining routine; and FIG. 7 shows a weighted-value determining routine.

In FIG. 5, at Step S1 (hereinafter, "Step" is omitted, if appropriate) corresponding to the blood-pressure-abnormality judging means 104, the control device judges whether each estimated blood-pressure value $E_{SYS}$ is smaller than a prescribed abnormal-blood-pressure-decrease judgment value, $A_L$. If a positive judgment is made at S1, the control goes to S2 where the control device determines a maximal water-remove-rate decrease amount, e.g., −0.2 l/h. However, if a negative judgment is made at S1, the control goes to S3 to judge whether the estimated blood-pressure value $E_{SYS}$ is greater than a prescribed abnormal-blood-pressure-increase judgment value, $A_H$. If a positive judgment is made at S3, the control goes to S4 where the control device determines a maximal water-remove-rate increase amount, e.g., +0.2 l/h. However, if a negative judgment is made at S3, the control goes to S5 corresponding to the weighted-value determining means 112. At S5, the control device determines, for each of a plurality of sorts of blood-pressure-change-related information, a weighted value corresponding to a change of the each sort of blood-pressure-change-related information, and determines an evaluation value P equal to a sum of the respective weighted values determined for the plurality of sorts of blood-pressure-change-related information that have been read in at a step, not shown.

FIG. 6 is for explaining, in more detail, the weighted-value determining routine implemented at S5. At SA1, the control device judges whether the hematocrit HCT has changed. If a positive judgment is made at SA1, the control goes to SA2 where the control device determines a weighted value corresponding a change of the hematocrit HCT. On the other hand, if a negative judgment is made at SA1, the control goes to SA3 to judge whether the circulation blood volume BV has changed. If a positive judgment is made at SA3, the control goes to SA4 to determine a weighted value corresponding a change of the circulation blood volume BV. On the other hand, if a negative judgment is made at SA3, the control goes to SA5 to judge whether the volumetric-pulse-wave amplitude AMP has changed. If a positive judgment is made at SA5, the control goes to SA6 to determine a weighted value corresponding a change of the volumetric-pulse-wave amplitude AMP. On the other hand, if a negative judgment is made at SA5, the control goes to SA7 to judge whether the estimated blood-pressure value $E_{SYS}$ has changed. If a positive judgment is made at SA7, the control goes to SA8 to determine a weighted value corresponding a change of the estimated blood-pressure value $E_{SYS}$. On the other hand, if a negative judgment is made at SA7, the control goes to SA9 to judge whether the low-frequency component DTLF has changed. If a positive judgment is made at SA9, the control goes to SA10 to determine a weighted value corresponding a change of the low-frequency component DTLF. On the other hand, if a negative judgment is made at SA9, the control goes to SA11 to judge whether the high-frequency component RRHF has changed. If a positive judgment is made at SA11, the control goes to SA12 to determine a weighted value corresponding a change of the high-frequency component RRHF. On the other hand, if a negative judgment is made at SA11, the control goes to SA13 to judge whether the pressoreceptor-reflex sensitivity BRS (=RRHF/DTLF) has changed. If a positive judgment is made at SA13, the control goes to SA14 to determine a weighted value corresponding a change of the pressoreceptor-reflex sensitivity BRS. On the other hand, if a negative judgment is made at SA13, or if a weighted value is determined at SA14, the control goes to SA15 to calculate a summarized evaluation value P equal to a sum of all the determined weighted values.

Back to FIG. 5, after the evaluation value P is determined at S5, the control goes to S6 corresponding to the water-remove-rate-control-amount determining means 114. At S6, the control device determines, based on the evaluation value P, a water-remove-rate control amount to change the water-remove rate correspondingly to the respective changes of the above described sorts of blood-pressure-change-related information, as shown in FIG. 7. More specifically described, at SB1 of FIG. 7, the control device judges whether the evaluation value P is greater than a second upper-limit judgment value, e.g., +20. If a positive judgment is made at SB1, the control goes to SB2 to determine a large water-remove-rate increase amount, e.g., +0.2 l/h. On the other hand, if a negative judgment is made at SB1, the control goes to SB3 to judge whether the evaluation value P is not greater than the second upper-limit judgment value and greater than a first upper-limit judgment value, e.g., +10. If a positive judgment is made at SB3, the control goes to SB4 to determine a small water-remove-rate increase amount, e.g., +0.1 l/h. On the other hand, if a negative judgment is made at SB3, the control goes to SB5 to judge whether the evaluation value P is not greater than the first upper-limit judgment value and greater than a first lower-limit judgment value, e.g., −10. If a positive judgment is made at SB5, the control goes to SB6 to determine zero as the water-remove-rate control amount, i.e., maintains the current water-remove rate. On the other hand, if a negative judgment is made at SB5, the control goes to SB7 to judge whether the evaluation value P is not greater than the first lower-limit judgment value and greater than a second lower-limit judgment value, e.g., −20. If a positive judgment is made at SB7, the control goes to SB8 to determine a small water-remove-rate decrease amount, e.g., −0.1 l/h. On the other hand, if a negative judgment is made at SB7, the control goes to SB9 to judge whether the evaluation value P is not greater than the second lower-limit judgment value, e.g., −20. If a positive judgment is made at SB9, the control goes to SB10 to determine a large water-remove-rate decrease amount, e.g., −0.2 l/h. On the other hand, if a negative judgment is made at SB9, the current control cycle according to the present routine is finished.

Back to FIG. 5, after Step S6 is implemented as described above, the control goes to S7 corresponding to the control-amount outputting means 116. At S7, the control device outputs the water-remove-rate control amount determined at S6, so as to control the rotation speed of the negative-pressure pump 72 of the water-remove control device 74 and thereby change the water-remove rate.

As is apparent from the foregoing description of the preferred embodiment, the blood-pressure-change-related-information obtaining means 110 obtains a plurality of sorts of blood-pressure-change-related information each of which is related to a change (e.g., a decrease) of a blood pressure of a patient during a dialysis operation, and the water-remove-rate control means 108 controls the water-remove rate of the dialyzer 70 based on the plurality of sorts of blood-pressure-change-related information according to the pre-stored control formula, i.e., evaluating formula. Thus, the present apparatus 4 can automatically control the water-remove rate so as to efficiently remove water from blood of the patient, without causing an abrupt blood-pressure decrease in the patient. Therefore, a skillful medical specialist such as a doctor need not adjust the water-remove rate so frequently, and consequently only a relatively small number of medical specialists are needed as compared with a number of dialyzing apparatuses used, and additionally each dialysis operation costs low.

In the illustrated embodiment, the blood-pressure-change-related-information obtaining means 110 obtains the blood-flow parameter that reflects the flow rate of blood of the patient; the autonomic-nerve parameter that reflects the activity of autonomic nerve of the patient; the blood-vessel parameter that reflects the degree of expansion of blood vessels of the patient; and the blood-viscosity parameter that reflects the viscosity of blood of the patient and, based on those parameters, the water-remove rate is controlled. Thus, the present apparatus 4 can operate the dialyzer 70 at an appropriate water-remove rate that corresponds to the blood flow rate, autonomic-nerve activity, blood-vessel expansion degree, and blood viscosity of the patient that are closely related to a blood-pressure decrease of the patient during the dialysis operation. Accordingly, the present apparatus 4 can efficiently remove water from the blood of the patient, without causing an abrupt blood-pressure decrease in the patient.

In the illustrated embodiment, the water-remove-rate control means 108 includes the weighted-value determining means 112 which determines, for each of the plurality of sorts of blood-pressure-change-related information, a weighted value corresponding to a change of the each sort of blood-pressure-change-related information; and the water-remove-rate-control-amount determining means 114 which determines the water-remove-rate control amount based on the sum of the respective weighted values determined for the plurality of sorts of blood-pressure-change-related information, and controls the water-remove rate of the dialyzer 70 according to the water-remove-rate control amount determined by the water-remove-rate-control-amount determining means 114. Since, for each of the plurality of sorts of blood-pressure-change-related information, a weighted value corresponding to a change of the each sort of blood-pressure-change-related information is determined, and the water-remove rate of the dialyzer is controlled according to a water-remove-rate control amount determined based on a sum of the respective weighted values determined for the plurality of sorts of blood-pressure-change-related information. Thus, the present apparatus can more efficiently remove water from the blood of the patient, without causing an abrupt blood-pressure decrease in the patient.

While the present invention has been described in detail in its preferred embodiment, by reference to the drawings, the invention may otherwise be embodied.

For example, in the illustrated embodiment, the plurality of sorts of blood-pressure-change-related information each of which is related to the change of blood pressure of the patient undergoing the dialysis operation, include the blood-flow parameter (i.e., the systemic-circulation blood volume BV or the volumetric-pulse-wave amplitude AMP) that reflects the flow rate of blood of the patient 80; the autonomic-nerve parameter (i.e., the low-frequency component DTLF, the high-frequency component RRHF, or the pressoreceptor-reflex sensitivity BARS) that reflects the activity of autonomic nerve of the patient 80; the blood-vessel parameter (i.e., the estimated blood-pressure value $E_{SYS}$, the pulse-wave propagation time DT, or the pulse-wave propagation velocity PUV) that reflects the degree of expansion of blood vessels of the patient 80; and the blood-viscosity parameter (i.e., the hematocrit HCT) that reflects the viscosity of blood of the patient 80. However, it is possible to employ only a portion (two or more) of the above parameters or alternatively employ different parameters than the above parameters.

Each of the above parameters may be measured in a different method than the previously-described method. For example, the pulse-wave propagation velocity PUV may be determined based on a time difference between a time of detection of a second heart sound and a time of detection of a rising point of a pulse wave detected by a pressure-pulse-wave sensor worn on a skin above a prescribed portion of an artery of a patient.

It is to be understood that the present invention may be embodied with other changes, improvements and modifications that may occur to a person skilled in the art without departing from the spirit and scope of the invention.

What is claimed is:

1. A dialyzing apparatus comprising:
   a dialyzer which removes water from blood of a patient at a water-remove rate during a dialysis operation;
   a blood-pressure-change-related-information obtaining device which obtains a plurality of sorts of blood-pressure- change-related information each of which is related to a change of a blood pressure of the patient during the dialysis operation; and
   a water-remove-rate control device which comprises (a) a weighted-value determining means for determining, for each of the plurality of sorts of blood-pressure-change-related information, a weighted value corresponding to a change of said each sort of blood-pressure-change-related information; (b) a water-remove-rate-control-amount determining means for determining a water-remove-rate control amount based on a sum of the respective weighted values determined for the plurality of sorts of blood-pressure-change-related information; and (c) a control means for controlling the water-remove rate of the dialyzer, according to the water-remove-rate control amount determined by the water-remove-rate-control-amount determining means.

2. A dialyzing apparatus according to claim 1, wherein the blood-pressure-change-related-information obtaining device obtains a blood-flow parameter that reflects a flow rate of a blood of the patient; an autonomic-nerve parameter that reflects an activity of an autonomic nerve of the patient; a blood-vessel parameter that reflects a degree of expansion of a blood vessel of the patient; and a blood-viscosity parameter that reflects a viscosity of the blood of the patient.

3. A dialyzing apparatus according to claim 2, wherein the blood-flow parameter comprises at least one of a systemic-circulation blood volume that is estimated based on a hematocrit that is optically detected from the blood circulating during the dialysis operation, and an amplitude of a volumetric pulse wave, such as a photoelectric pulse wave, a finger-tip pulse wave, or an impedance pulse wave, that is detected by a sensor which is adapted to be worn on a skin of the patient.

4. A dialyzing apparatus according to claim 2, wherein the autonomic-nerve parameter comprises at least one of a low-frequency component of fluctuations of respective blood-pressure values that are determined in synchronism with respective heartbeats of the patient, a high-frequency component of fluctuations of respective pulse-period values that are determined in synchronism with the respective heartbeats of the patient, and a pressoreceptor-reflex sensitivity that is defined as a ratio of one of the high-frequency component and the low- frequency component to the other of the high-frequency component and the low-frequency component.

5. A dialyzing apparatus according to claim 2, wherein the blood-vessel parameter comprises at least one of an estimated blood-pressure value that is determined based on a pulse-wave propagation velocity at which a pulse wave propagates through an artery of the patient, in synchronism with each heartbeat of the patient, and a pulse-wave propagation time, and a pulse-wave propagation velocity, that are determined by a pulse-wave propagation-velocity determining means in synchronism with each heartbeat of the patient.

6. A dialyzing apparatus according to claim 2, wherein the blood-viscosity parameter comprises a hematocrit that is optically detected from the blood circulating during the dialysis operation.

* * * * *